US011318189B1

(12) United States Patent
Soon-Shiong et al.

(10) Patent No.: US 11,318,189 B1
(45) Date of Patent: May 3, 2022

(54) IL-15 AGONIST DRUG COMBINATIONS FOR IMMUNE THERAPY

(71) Applicant: NantCell, Inc., Culver City, CA (US)

(72) Inventors: Patrick Soon-Shiong, Los Angeles, CA (US); John Lee, Topanga, CA (US)

(73) Assignee: NANTCELL, INC., Culver City, CA (US)

( * ) Notice: Subject to any disclaimer, the term of this patent is extended or adjusted under 35 U.S.C. 154(b) by 0 days.

(21) Appl. No.: 17/313,285

(22) Filed: May 6, 2021

Related U.S. Application Data

(60) Provisional application No. 63/024,181, filed on May 13, 2020.

(51) Int. Cl.

| | |
|---|---|
| ***A61K 38/20*** | (2006.01) |
| ***A61K 31/545*** | (2006.01) |
| ***A61K 31/546*** | (2006.01) |
| ***A61K 9/00*** | (2006.01) |

(52) U.S. Cl.
CPC ........ *A61K 38/2086* (2013.01); *A61K 9/0019* (2013.01); *A61K 31/545* (2013.01); *A61K 31/546* (2013.01)

(58) Field of Classification Search
CPC .................................................. A61K 38/2086
See application file for complete search history.

(56) References Cited

U.S. PATENT DOCUMENTS

| | | | |
|---|---|---|---|
| 5,916,596 | A | 6/1999 | Desai et al. |
| 6,506,405 | B1 | 1/2003 | Desai et al. |
| 6,537,579 | B1 | 3/2003 | Desai et al. |
| 9,328,159 | B2 | 5/2016 | Wong et al. |
| 2009/0238791 | A1 | 9/2009 | Jacques et al. |
| 2013/0142755 | A1 | 6/2013 | Boyman et al. |

OTHER PUBLICATIONS

GYSSENS (Drugs, 1999, vol. 57, No. 2, pp. 175-185) (Year: 1999).*
Guo, Y. et al., "Immunobiology of the IL-15-IL-15Rα Complex as an Antitumor and Antiviral Agent," Cytokine Growth Factor Rev., 38: 10-21 (2017).
Zyzynska-Granica, B., et al., "The anti-inflammatory potential of cefazolin as common gamma chain cytokine inhibitor," Scientific Reports, 10(2886): 1-12 (2020).
Chaperon, E.A. and Sanders, Jr., W.E., "Suppression of Lymphocyte Resonses by Cephalosporins," Infection and Immunity, 19(2): 378-384 (1978).

* cited by examiner

*Primary Examiner* — James D. Anderson
(74) *Attorney, Agent, or Firm* — Harness Dickey & Pierce P.L.C.

(57) ABSTRACT

Methods and pharmaceutical combinations for preventing, reducing the occurrence of, and/or treating an infection in a subject are provided herein. The method includes administering to the subject a therapeutically effective amount of an IL-15 agonist after or concomitantly with administration of a therapeutically effective amount of an antibiotic to the subject. The pharmaceutical combination includes an IL-15 agonist and an antibiotic.

26 Claims, 1 Drawing Sheet

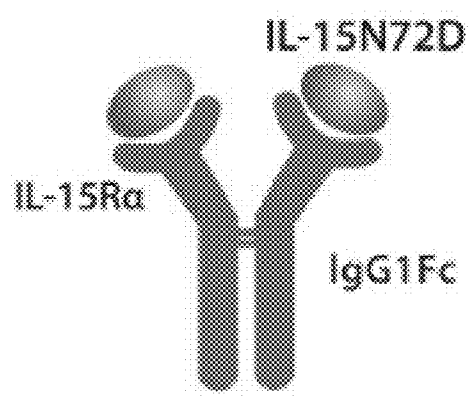
IL-15N72D
IL-15Ra
IgG1Fc

IL-15 AGONIST DRUG COMBINATIONS FOR IMMUNE THERAPY

CROSS-REFERENCE TO RELATED APPLICATIONS

This application claims the benefit of and priority to U.S. Provisional Application No. 63/024,181, filed on May 13, 2020, the entire contents of which are hereby incorporated herein by reference.

FIELD

The present disclosure relates to immune stimulating compositions and methods comprising an IL-15 agonist in combination with an antibiotic for the prevention and/or treatment of an infection, for example, following a surgical procedure.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Pro-inflammatory cytokines, such as IL-15, play a critical role in the innate and adaptive immune responses. Many immune cells, including lymphocytes (T and B cells), NK cells, monocytes, macrophages, dendritic cells, neutrophils, eosinophils, and mast cells express the IL-15 receptor, IL-15Rα, and are sensitive to IL-15 in the microenvironment. Binding of IL-15 to IL-15Rα activates the intracellular JAK/STAT signaling pathway, leading to systemic immunomodulatory effects. IL-15 plays a role in the innate and adaptive immune response to various viral infections. In vivo, IL-15 is typically trans-presented with IL-15Ra to activate immune cells.

U.S. 2009/0238791 reports an IL-15/IL-15Ra fusion protein comprising an IL-15Ra sushi domain.

U.S. 2013/0142755 reports an IL-15/IL-15Rα-IgG1-Fc complex that activates NK, NTK and memory $CD8^+$ T cells.

U.S. Pat. No. 9,328,159 reports an IL-15/IL-15Rα-IgG1-Fc complex where the IL-15 contains an N72D point mutation. This superagonist is also known as nogapendekin alfa-inbakicept (NAI).

It is common practice to prophylactically administer an antibiotic to a patient prior to a surgical procedure to prevent and/or lower the occurrence of an infection following surgery. However, some antibiotics, such as cephalosporins, have been shown to suppress immune response. For example, cephalosporins have been shown to suppress lymphocyte response. See Chaperon, E. A. and Sanders, W. E. (1978) *Infect Immun,* 19(2):378-384. Additionally, the antibiotic, cefazolin, has been shown to exhibit inhibitory activity of cytokine receptors for cytokines, such as IL-2, IL-15, IL-4, and IL-21. See Żyżyńska-Granica, B. et al. (2020) *Sci Rep,* 10(1):2866; DOI: 10.1038/s41598-020-59798-3.

Consequently, there is a need to provide improved compositions and methods for immune stimulants and antibiotics to prevent infection and/or reduce the occurrence of infection, for example, following a surgical procedure.

SUMMARY

Various pharmaceutical combinations and methods that employ an antibiotic, e.g., a cephalosporin, and an IL-15-based therapeutic, e.g., a nogapendekin alfa-inbakicept (NAI), for the prevention of an infection, the reduction of an occurrence of an infection, and/or the treatment of an infection are disclosed herein, where the IL-15-based therapeutic is administered after or concomitantly with the antibiotic.

In one aspect of the present disclosure, a method for preventing, reducing the occurrence of, and/or treating an infection in a subject (e.g., a human) in need thereof is provided. The method includes administering to the subject a therapeutically effective amount of an IL-15 agonist after or concomitantly with administration of a therapeutically effective amount of an antibiotic to the subject.

The IL-15 agonist may be administered to the subject prior to the subject undergoing a surgical procedure and/or after the subject has undergone the surgical procedure. The IL-15 agonist can be administered at least about 1 minute before the surgical procedure begins. Additionally or alternatively, the IL-15 agonist can be administered to the subject less than or equal to about 12 hours after the surgical procedure ends.

In another aspect of the present disclosure, a pharmaceutical combination is provided herein. The pharmaceutical combination includes an IL-15 agonist and an antibiotic.

In another aspect of the present disclosure, a pharmaceutical combination for use in preventing or treating an infection in a subject is provided herein. The pharmaceutical combination includes an IL-15 agonist and an antibiotic.

Preferably, the IL-15 agonist in the contemplated methods and combinations is nogapendekin-alfa-inbakicept (NAI), also known as N-803. It is further contemplated that the step of administering comprises subcutaneous injection or intravenous administration of the IL-15 agonist, and where appropriate, the step of administering comprises multiple administrations of the IL-15 agonist (e.g., twice per week, three or more times per week, etc.). Suitable doses of the IL-15 agonist may be between 10 μg and about 500 μg per dose, for example, about 50 μg.

The antibiotic in the contemplated methods and combinations may be a cephalosporin. For example, the antibiotic may be selected from the group consisting of cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, oxacephem, latamoxef, cefclidine, cefepime, cefiderocol, cefluprenam, cefoselis, cefozopran, cefpirome, cefquinome, flomoxef, ceftobiprole, ceftaroline, ceftolozane, and a combination thereof. Preferably, the antibiotic may be cefazolin.

Various objects, features, aspects, and advantages will become more apparent from the following detailed description of preferred embodiments, along with the accompanying drawing in which like numerals represent like components.

BRIEF DESCRIPTION OF THE DRAWINGS

FIG. 1 is a representation of NAI (N-803).

DETAILED DESCRIPTION

I. Definitions

The following definitions refer to the various terms used above and throughout the disclosure.

The term "antibiotic" refers to compounds or compositions that can destroy, reduce the viability of, and/or inhibit the growth of a microorganism (e.g., bacteria). Antibiotics can be formulated in the same formulation as the IL-15 agonist, or in a different formulation for concurrent or sequential administration with the IL-15 agonist.

The term "bacterial infection" is not particularly limited and refers to a condition in which a subject is infected with a bacterium. This includes the excessive growth of bacteria which are normally present in or on the body of a subject, such as a mammal. More generally, a bacterial infection can be any situation in which the presence of a bacterial population(s) is damaging to a host subject, for example, excessive numbers of a bacterial population are present in or on a subject's body, and/or when the effects of the presence of a bacterial population(s) is damaging the cells or other tissue of a subject. The infection may be symptomatic or asymptomatic. Particular embodiments of bacterial infections include infections caused by Gram-positive bacterium and Gram-negative bacterium. Examples of Gram-positive bacterium include, but are not limited to, *Streptococcus, Staphylococcus, Enterococcus, Corynebacterium, Listeria, Bacillus*, and *Clostridium*. Examples of Gram-negative bacterium include, but are not limited to, *Acinetobacter, Klebsiella, Pseudomonas*, and *Escherichia.*

The term "concomitant" or "concomitantly" includes administering an agent (e.g., IL-15 agonist) in the presence of a further agent (e.g., an antibiotic). Concomitant administration in a therapeutic treatment method includes methods in which a first, second, third, or additional agents are co-administered. Concomitant administration also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent (e.g., an antibiotic) and a second actor may administer to the subject a second agent (e.g., IL-15 agonist), and the administering steps may be executed at the same time, or nearly the same time. The actor and the subject may be the same entity (e.g., human). Thus, the term embraces both simultaneous administration and substantially simultaneous administration, i.e., at about the same time.

The term "effective amount" or "therapeutically effective amount" refers to the amount and/or dosage, and/or dosage regime of one or more agent(s) necessary to bring about the desired result e.g., an amount sufficient to prevent an infection in a subject, an amount sufficient to reduce the occurrence of an infection in a subject, and/or an amount sufficient to treat an infection in a subject.

The term "IL-15 agonist" or "IL-15 agonist or derivative thereof" refers to a compound or molecule that binds to and activates the IL-15 receptor ("IL-15Rα"). The type of compound or molecule of the IL-15 agonist is not particularly limited so long as it binds to and activates the IL-15Rα. The IL-15 agonist may be a peptide, protein, small molecule (e.g., a pharmaceutical drug), or oligonucleotide. The peptide or proteins may be a single amino acid sequence or two or more sequences bound via covalent attachments (e.g., disulfide bonds) or non-covalent attachments (e.g., hydrophilic or hydrophobic interactions, hydrogen bonds). In a particular embodiment, the IL-15 agonist is an antibody, modified antibody, chimeric antibody, or a derivative thereof. In a further embodiment, the IL-15 agonist is a superagonist complex, such as an IL-15 derivative bound to an IL-15Rα/IgG1 Fc fusion protein, also known as NAI. NAI is also known in the literature as N-803 or ALT-803. U.S. Pat. No. 9,328,159 describes NAI and is incorporated herein by reference in its entirety.

Binding of the IL-15 agonist to the IL-15Ra induces a signal to downstream elements to activate the IL-15 signaling pathway and activate the cell. Cells expressing IL-15Ra include, but are not limited to, T cells, NK cells, monocytes, macrophages, dendritic cells, keratinocytes, fibroblasts, myocytes, and nerve cells. Guo, et al. *Cytokine Growth Factor Rev.,* 2017. Binding of the IL-15 agonist to the IL-15Rα propagates a signal through the IL-15Rα (e.g., via a conformational change) that initiates the IL-15 signaling pathway to activate an immune response, such as an antiviral response.

The term "derivative" refers to a compound that is structurally similar to the reference compound such that it retains some, all, or more of its biological effect. For example, a derivative of an IL-15 agonist includes compounds or molecules that partially activate the IL-15Rα (e.g., a partial agonist), fully activate the IL-15Rα (e.g., a full agonist), or activate the IL-15Rα to a higher degree than the reference compound or molecule (e.g., a super agonist).

The terms "subject", "individual", and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments the subject may not be under the care or prescription of a physician or other health worker.

The term "surgical procedure" refers to collectively all therapeutic and diagnostic procedures, including procedures requiring an incision made on a subject as well as endoscopic procedures.

The term "treat" and "treatment" refers to a method for reducing, inhibiting, or otherwise ameliorating an infection by administering a therapeutically effective amount of an IL-15 agonist after or concomitantly with administration of a therapeutically effective amount of an antibiotic.

II. Pharmaceutical Combinations

Pharmaceutical combinations including an IL-15 agonist or a derivative thereof and an antibiotic are provided herein.

In any embodiment, the IL-15 agonist is an antibody, modified antibody, chimeric antibody, or a derivative thereof. In a further embodiment, the IL-15 agonist is a superagonist complex, such as an IL-15 derivative bound to an IL-15Rα/IgG1 Fc fusion protein, also known as NAI. NAI is also known in the literature as N-803 or ALT-803. In a particular embodiment, the IL-15 agonist is NAI.

The antibiotic may be any suitable antibiotic known in the art. For example, the antibiotic may be in an antibiotic class selected from the group consisting of a penicillin, a tetracycline, a cephalosporin, a quinolone, a lincomycin, a macrolide, a glycopeptide, an aminoglycoside, a carbapenem, or a combination thereof. In a particular embodiment, the antibiotic may be a penicillin, a glycopeptide, a cephalosporin, or a combination thereof. Examples of penicillin antibiotics include, but are not limited to, penicillin G, penicillin K, penicillin N, penicillin O, penicillin V, methicillin, nafcillin, oxacillin, cloxacillin, dicloxacillin, flucloxacillin, ampicillin, amoxicillin, pivampicillin, hetacillin, bacampicillin, metampicillin, talampicillin, epicillin, carbenicillin, ticarcillin, temocillin, mezlocillin, piperacillin, azlocillin, clavulanic acid, sulbactam, tazobactam, and combinations thereof. Examples of glycopeptide antibiotics include, but are not limited to vancomycin, teicoplanin, telavancin, ramoplanin, decaplanin, corbomycin, complestatin, bleomycin, and combinations thereof. Examples of cephalosporins include, but are not limited to cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, oxacephem, latamoxef, cefclidine, cefepime, cefiderocol, cefluprenam, cefoselis, cefozopran, cefpirome, cefquinome, flomoxef, ceftobiprole, ceftaroline, ceftolozane, and combinations thereof. In a particular embodiment, the antibiotic is cefazolin.

In any embodiment, an IL-15 agonist, an antibiotic, or a combination thereof may be formulated with a pharmaceutically-acceptable carrier to form a pharmaceutical composition. For example, NAI may be formulated with a pharmaceutically-acceptable carrier and a cephalosporin antibiotic (e.g., cefazolin) may be formulated with a pharmaceutically-acceptable carrier. It is contemplated herein that the IL-15 agonist and the antibiotic may be packaged separately or together in the pharmaceutical combination.

Separate dosage forms/active agents can optionally be co-packaged, for example in a single container or in a plurality of containers within a single outer package or co-presented in separate packaging ("common presentation"). As an example of co-packaging or common presentation, a kit is contemplated comprising, in separate containers, an IL-15 agonist, such as NAI or a derivative thereof, and one or more of the further active agents disclosed herein. In another example, the IL-15 agonist, such as NAI or a derivative thereof, and the one or more of the further active agents are separately packaged and available for sale independently of one another, but are co-marketed or co-promoted for use according to the invention. The separate dose forms/active agents may also be presented to a subject separately and independently, for use according to the invention.

The combinations or compositions disclosed herein may be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional, and intracranial injection or infusion techniques. In a particular embodiment, the combinations or compositions are administered orally, intraperitoneally, subcutaneously, or intravenously.

The combinations or compositions disclosed herein may be orally administered in any orally acceptable dosage form including, but not limited to, capsules, tablets, troches, elixirs, suspensions, syrups, wafers, chewing gums, aqueous suspensions, or solutions.

The oral compositions disclosed herein may contain additional ingredients such as: a binder, such as microcrystalline cellulose, gum tragacanth or gelatin; an excipient, such as starch or lactose; a disintegrating agent, such as alginic acid, corn starch and the like; a lubricant, such as magnesium stearate; a glidant, such as colloidal silicon dioxide; and a sweetening agent, such as sucrose or saccharin or flavoring agent, such as peppermint, methyl salicylate, or orange flavoring. When the dosage unit form is a capsule, it may additionally contain a liquid carrier, such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

Additionally or alternatively, the combinations or compositions disclosed herein may be formulated for parenteral administration where the active ingredient (e.g., IL-15 agonist, antibiotic) may be incorporated into a solution or suspension. The solutions or suspensions may also include the following components: a sterile diluent, such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers such as acetates, citrates or phosphates and agents for the adjustment of tonicity, such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterilizing procedures, such as filtration, may then follow. Typically, dispersions are made by incorporating the compound into a sterile vehicle which also contains the dispersion medium and the required other ingredients as indicated above. In the case of a sterile powder, the particular methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents, such as lecithin; polyoxyethylene stearate; and the like. The carrier may also contain adjuvants such as preserving stabilizing, wetting, and emulsifying agents and the like together with a penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

U.S. Pat. Nos. 5,916,596; 6,506,405; and 6,537,579 teach the preparation of nanoparticles from the biocompatible polymers, such as albumin. Thus, provided herein are methods for the formation of nanoparticles by a solvent evaporation technique from an oil-in-water emulsion prepared under conditions of high shear forces (e.g., sonication, high pressure homogenization, or the like).

Additionally or alternatively, the combinations or compositions disclosed herein may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Additionally or alternatively, the combinations or compositions disclosed herein may be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the combinations or compositions may be formulated in a suitable ointment containing the active component (e.g., IL-15 agonist, antibiotic) suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Additionally or alternatively, the compositions or combinations can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Additionally or alternatively, the combinations or compositions disclosed herein may be formulated for ophthalmic use as micronized suspensions in isotonic, pH adjusted sterile saline, or as solutions in isotonic, pH adjusted sterile saline, either with or without a preservative such as benzylalkonium chloride. Additionally or alternatively, for ophthalmic uses, the combinations or compositions may be formulated in an ointment such as petrolatum.

Additionally or alternatively, the combinations and compositions disclosed herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

III. Methods of Use

Additionally, an IL-15 agonist as described herein and/or pharmaceutical compositions or combinations comprising an IL-15 agonist as described herein and an antibiotic as described herein, can be used to prevent, reduce the occurrence of, and/or treat an infection in a subject in need thereof. A method is provided herein including administering to a subject in need thereof a therapeutically effective amount of an IL-15 agonist. The therapeutically effective amount of the IL-15 agonist can be administered after or concomitantly with administration of a therapeutically effective amount of an antibiotic to the subject. Administration of the IL-15 agonist may support a NK and T cell immune response to the infection. It is contemplated herein that the IL-15 agonist and the antibiotic may be administered by the same or different individuals. The IL-15 agonist, the antibiotic, or a combination thereof, may be administered or otherwise provided in a composition, such as a pharmaceutical composition further comprising one or more pharmaceutically acceptable excipients as described herein. Additional pharmaceutical ingredients may also be administered concurrent or sequential with the IL-15 agonist. In further embodiments, the infection can be inhibited in vitro or in vivo.

In any embodiment, the IL-15 agonist may be administered to the subject prior to the subject undergoing a surgical procedure, after the subject has undergone the surgical procedure, or both. For example, the IL-15 agonist may be administered to the subject at least about 1 minute before the surgical procedure begins, at least about 10 minutes before the surgical procedure begins, at least about 30 minutes before the surgical procedure begins, at least about 1 hour before the surgical procedure begins, at least about 3 hours before the surgical procedure begins, at least about 6 hours before the surgical procedure begins, at least about 12 hours before the surgical procedure begins, or about 24 hours before the surgical procedure begins; or from about 1 minute to about 24 hours before the surgical procedure begins, or about 1 minute to about 12 hours before the surgical procedure begins, or about 1 minute to about 1 hour before the surgical procedure begins. Additionally or alternatively, the IL-15 agonist, may be administered less than or equal to about 24 hours after the surgical procedure ends, less than or equal to about 12 hours after the surgical procedure ends, less than or equal to about 6 hours after the surgical procedure ends, less than or equal to about 3 hours after the surgical procedure ends, less than or equal to about 1 hour after the surgical procedure ends, less than or equal to about 30 minutes after the surgical procedure ends, less than or equal to about 10 minutes after the surgical procedure ends, less than or equal to about 1 minute after the surgical procedure ends; or from about 1 minute to about 24 hours after the surgical procedure ends, about 1 minute to about 12 hours after the surgical procedure ends, or about 1 minute to about 1 hour after the surgical procedure ends.

In further embodiments, the therapeutically effective amount of the IL-15 agonist and/or the therapeutically effective amount of the antibiotic, is an amount that prevents, reduces the occurrence of, and/or treats an infection. In any embodiment, the therapeutically effective amount of the IL-15 agonist ranges between about 10 μg to about 500 μg per dose. In a particular embodiment, the therapeutically effective amount of the IL-15 agonist is about 50 μg per dose, about 100 μg per dose, about 200 μg dose, or about 400 μg per dose.

The therapeutically effective amount of the IL-15 agonist and/or the antibiotic may be administered one or more times depending on the infection and severity of the infection. For example, the IL-15 agonist and/or the antibiotic may be administered once per week, twice per week, three or more times per week, one or more times per day, less than once per week, once every two weeks, once every three weeks, once every four or more weeks, semi-monthly, monthly, or bimonthly. In any embodiment, the IL-15 agonist and/or the antibiotic may be administered in a form as described above, for example, subcutaneously or intravenously.

The infection may be a bacterial infection. It is contemplated herein that the bacterial infection may be caused by a Gram-positive bacterium and/or a Gram-negative bacterium. Examples of Gram-positive bacterium include, but are not limited to, *Streptococcus* species, *Staphylococcus* species, *Enterococcus* species, *Corynebacterium* species, *Listeria* species, *Bacillus* species, *Clostridium* species, and combinations thereof. Examples of Gram-negative bacterium include, but are not limited to, *Acinetobacter* species, *Klebsiella* species, *Pseudomonas* species, *Escherichia* species, and combinations thereof. *Staphylococcus* species include, but are not limited to, *Staphylococcus Aureus*, Methicillin Resistant *Staphylococcus Aureus* (MRSA), and Vancomycin Resistant *Staphylococcus Aureus* (VRSA). *Enterococcus* species include, but are not limited to, *Enterococcus faecalis, Enterococcus faecium*, and Vancomycin Resistant Enterococci (VRE).

EXAMPLES

The following example is provided to further illustrate the invention disclosed herein but, of course, should not be construed as in any way limiting its scope.

Example 1: NAI

NAI is an IL-15 superagonist complex comprising the IL-15N72D derivative bound to an IL-15Rα/IgG1 Fc fusion protein (previously described in U.S. Pat. No. 9,328,159) and can be seen in FIG. 1.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Particular embodiments of this invention are described herein, including the best mode known to the inventors for carrying out the invention. Variations of those particular embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating a bacterial infection in a subject in need thereof, the method comprising administering to the subject a therapeutically effective amount of nogapendekin-alfa-inbakicept (NAI) prior to the subject undergoing a surgical procedure, but after or concomitantly with administration of a therapeutically effective amount of an antibiotic to the subject.

2. A method for treating a bacterial infection in a subject in need thereof, the method comprising administering to the subject a therapeutically effective amount of NAI after the subject has undergone a surgical procedure, and after or concomitantly with administration of a therapeutically effective amount of an antibiotic to the subject.

3. The method of claim 1, wherein NAI is administered to the subject at least about 1 minute before the surgical procedure begins.

4. The method of claim 2, wherein NAI is administered to the subject less than or equal to about 12 hours after the surgical procedure ends.

5. The method of claim 2, wherein NAI is administered more than once.

6. The method of claim 5, wherein NAI is administered twice per week.

7. The method of claim 5, wherein NAI is administered three times or more per week.

8. The method of claim 2, wherein the therapeutically effective amount of NAI is between about 10 μg and about 500 μg per dose.

9. The method of claim 8, wherein the therapeutically effective amount of NAI is about 50 μg.

10. The method of claim 9, wherein NAI is administered subcutaneously or intravenously.

11. The method of claim 9, wherein the antibiotic is a cephalosporin.

12. The method of claim 9, wherein the antibiotic is cefazolin.

13. The method of claim 2, wherein the subject is a human.

14. A pharmaceutical combination comprising nogapendekin-alfa-inbakicept (NAI) and an antibiotic.

15. The pharmaceutical combination of claim 14, wherein the antibiotic is a cephalosporin.

16. The pharmaceutical combination of claim 14, wherein the antibiotic is selected from the group consisting of cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, oxacephem, latamoxef, cefclidine, cefepime, cefiderocol, cefluprenam, cefoselis, cefozopran, cefpirome, cefquinome, flomoxef, ceftobiprole, ceftaroline, ceftolozane, and a combination thereof.

17. The pharmaceutical combination of claim 14, wherein the antibiotic is cefazolin.

18. The method of claim 1, wherein NAI is administered more than once.

19. The method of claim 18, wherein NAI is administered twice per week.

20. The method of claim 18, wherein NAI is administered three times or more per week.

21. The method of claim 1, wherein the therapeutically effective amount of NAI is between about 10 μg and about 500 μg per dose.

22. The method of claim 21, wherein the therapeutically effective amount of NAI is about 50 μg.

23. The method of claim 22, wherein NAI is administered subcutaneously or intravenously.

24. The method of claim 22, wherein the antibiotic is a cephalosporin.

25. The method of claim 22, wherein the antibiotic is cefazolin.

26. The method of claim 1, wherein the subject is a human.

* * * * *